(12) United States Patent
Hayashi et al.

(10) Patent No.: US 8,940,312 B2
(45) Date of Patent: Jan. 27, 2015

(54) COMPOSITION CONTAINING POLYUNSATURATED FATTY ACID

(75) Inventors: Naoko Hayashi, Takatsuki (JP); Kenji Masuda, Takatsuki (JP)

(73) Assignee: Sunstar Inc., Osaka (JP)

( * ) Notice: Subject to any disclaimer, the term of this patent is extended or adjusted under 35 U.S.C. 154(b) by 0 days.

(21) Appl. No.: 13/978,960

(22) PCT Filed: Jan. 27, 2012

(86) PCT No.: PCT/JP2012/051751
§ 371 (c)(1),
(2), (4) Date: Jul. 10, 2013

(87) PCT Pub. No.: WO2012/102364
PCT Pub. Date: Aug. 2, 2012

(65) Prior Publication Data
US 2013/0287827 A1    Oct. 31, 2013

(30) Foreign Application Priority Data
Jan. 27, 2011    (JP) ................... 2011-015331

(51) Int. Cl.

| | | |
|---|---|---|
| *A61K 8/02* | (2006.01) | |
| *A61K 9/127* | (2006.01) | |
| *A61K 8/14* | (2006.01) | |
| *A61K 9/00* | (2006.01) | |
| *A61K 31/201* | (2006.01) | |
| *A61K 8/36* | (2006.01) | |
| *A61K 8/67* | (2006.01) | |
| *A61Q 19/02* | (2006.01) | |
| *A61K 8/92* | (2006.01) | |
| *A61K 31/355* | (2006.01) | |
| *A61K 8/55* | (2006.01) | |

(52) U.S. Cl.
CPC ............. *A61K 8/14* (2013.01); *A61K 9/0014* (2013.01); *A61K 9/127* (2013.01); *A61K 31/201* (2013.01); *A61K 8/361* (2013.01); *A61K 8/678* (2013.01); *A61Q 19/02* (2013.01); *A61K 8/92* (2013.01); *A61K 31/355* (2013.01); *A61K 8/55* (2013.01)
USPC .......................................... 424/401; 424/450

(58) Field of Classification Search
CPC ........ A61K 8/678; A61K 31/201; A61K 8/14
See application file for complete search history.

(56) References Cited

U.S. PATENT DOCUMENTS

2003/0103916 A1    6/2003    Imanaka et al.

FOREIGN PATENT DOCUMENTS

| JP | 63-72654 | 4/1988 |
|---|---|---|
| JP | 8-81326 | 3/1996 |
| JP | 8-104635 | 4/1996 |
| JP | 11-505818 | 5/1999 |
| JP | 2004-182673 | 7/2004 |
| JP | 2005-336127 | 12/2005 |
| JP | 2007-126438 | 5/2007 |
| JP | 2007-269683 | 10/2007 |
| JP | 2007-269684 | 10/2007 |
| JP | 2010-502733 | 1/2010 |
| WO | 98/56338 | 12/1998 |
| WO | 2008/030949 | 3/2008 |
| WO | WO 2008030949 | * 3/2008 |
| WO | 2008/093848 | 8/2008 |
| WO | WO 2008093484 | * 8/2008 |

OTHER PUBLICATIONS

International Search Report issued Mar. 19, 2012 in International (PCT) Application No. PCT/JP2012/051751.
Supplementary European Search Report issued May 28, 2014 in corresponding European Application No. 12739031.8.
Yasutami Shigeta et al., "Skin Whitening Effect of Linoleic Acid is Enhanced by Liposomal Formulations", Biol. Pharm. Bull., vol. 27, No. 4, Apr. 2004, pp. 591-594.
C. Anthony Hunt et al., "α-Tocopherol Retards Autoxidation and Prolongs the Shelf-Life of Liposomes", International Journal of Pharmaceutics, vol. 8, No. 2, Apr. 1981, pp. 101-110.
Office Action issued Jul. 21, 2014 in corresponding Chinese Application No. 201280006440.7, with English translation thereof.
The Production and Application of Antioxidants, p. 383, Jan. 2004.

* cited by examiner

*Primary Examiner* — Alton Pryor
(74) *Attorney, Agent, or Firm* — Wenderoth, Lind & Ponack, L.L.P.

(57) ABSTRACT

An object of the present invention is to provide a composition for external use comprising a polyunsaturated fatty acid having higher stability over time. The present invention provides the following composition, in which the stability over time of a polyunsaturated fatty acid is high.
A composition comprising a component (A) and a component (B) shown below, the component (B) being dispersed in a continuous phase that contains the component (A):
  (A) at least one member selected from the group consisting of tocopherol and phytic acid; and
  (B) liposomes containing a polyunsaturated fatty acid or a derivative thereof.

7 Claims, No Drawings

COMPOSITION CONTAINING POLYUNSATURATED FATTY ACID

TECHNICAL FIELD

The present invention relates to a composition (preferably a composition for external use) containing a polyunsaturated fatty acid.

BACKGROUND ART

Polyunsaturated fatty acids are mixed in compositions for external use (e.g., cosmetics and external-use pharmaceuticals) in anticipation of skin-whitening effect, etc. However, polyunsaturated fatty acids are known to have poor stability over time, and the polyunsaturated fatty acid content of the compositions decreases over time. Furthermore, compositions blended with polyunsaturated fatty acids may be colored or develop bad smells. Particularly in Japan, laws, regulations, etc., require compositions for external use containing a polyunsaturated fatty acid as an active ingredient to stably retain 90% or more of the polyunsaturated fatty acid based on the specified amount for three years after production. Therefore, the development of effective stabilization techniques has been desired. For example, the following techniques have been proposed to improve the stability over time of polyunsaturated fatty acids: a technique of mixing eugenol, isoeugenol, vitamin K, or the like (PTL 1); techniques of mixing esterified polyunsaturated fatty acids (PTL 2 to PTL 4); a technique of producing an aerosol comprising nitrogen gas and a content containing a highly unsaturated fatty acid-containing lipid (PTL 5); and a technique of producing an emulsion in which a polyunsaturated fatty acid is mixed with a specific amount of a dispersing agent, such as vitamin E (PTL 6).

CITATION LIST

Patent Literature

PTL 1: JP63-72654A
PTL 2: JP2007-126438A
PTL 3: JP2007-269683A
PTL 4: JP2007-269684A
PTL 5: JP8-81326A
PTL 6: JP2010-502733A

SUMMARY OF INVENTION

Technical Problem

An object of the present invention is to provide a composition for external use comprising a polyunsaturated fatty acid with higher stability over time.

Solution to Problem

As a result of extensive research in view of the above situation, the present inventors surprisingly found that a composition comprising a polyunsaturated fatty acid with excellent stability over time can be obtained by incorporating the polyunsaturated fatty acid or a derivative thereof into liposomes, dispersing the liposomes in a dispersion medium (continuous phase), and adding at least one member selected from the group consisting of tocopherol and phytic acid to the continuous phase. The present inventors made further improvements to achieve the present invention.

More specifically, the present invention includes a composition, etc., described in the following items:

Item 1. A composition comprising a component (A) and a component (B) shown below, the component (B) being dispersed in a continuous phase that contains the component (A):

(A) at least one member selected from the group consisting of tocopherol and phytic acid; and
(B) liposomes containing a polyunsaturated fatty acid or a derivative thereof.

Item 2. The composition according to item 1, wherein the tocopherol is at least one member selected from the group consisting of α-tocopherol, β-tocopherol, γ-tocopherol, δ-tocopherol, dl-α-tocopherol acetate, dl-α-tocopherol, and d-α-tocopherol acetate.

Item 3-1. The composition according to item 1 or 2, wherein the polyunsaturated fatty acid has 18 to 22 carbon atoms.

Item 3-2. The composition according to any one of items 1 to 3-1, wherein the polyunsaturated fatty acid has 2 to 6 double bonds.

Item 4. The composition according to any one of items 1 to 3-2, wherein the continuous phase contains at least phytic acid.

Item 5. The composition according to any one of items 1 to 4, wherein the continuous phase contains at least δ-tocopherol.

Item 6. The composition according to any one of items 1 to 5, wherein the continuous phase further contains at least one member selected from the group consisting of L-cystine and L-threonine. Item 7. The composition according to any one of items 1 to 6, wherein the liposomes also contain at least one member selected from the group consisting of tocopherol and phytic acid.

Item 8. The composition according to any one of items 1 to 7, which is a composition used for external application.

Item A-1. A method for whitening skin comprising the step of applying the composition according to any one of items 1 to 8 to the skin.

Item A-2. A therapeutic or cosmetic method for whitening skin comprising the step of applying the composition according to any one of items 1 to 8 to the skin.

Item B-1. The composition according to any one of items 1 to 8, which is used in skin whitening treatment.

Item C-1. Use of the composition according to any one of items 1 to 8 in the production of medicines for skin whitening treatment.

Advantageous Effects of Invention

In the composition for external use of the present invention, the polyunsaturated fatty acids contained in the liposomes have high stability over time. This enables effective use of the skin-whitening effect, etc., of the polyunsaturated fatty acids.

DESCRIPTION OF EMBODIMENTS

The composition of the present invention comprises the following components (A) and (B):

(A) at least one member selected from the group consisting of tocopherol and phytic acid; and
(B) liposomes containing a polyunsaturated fatty acid or a derivative thereof.

In the composition of the present invention, the component (B) is dispersed in a dispersion medium (continuous phase) that contains the component (A). That is, the composition of the present invention is a dispersion system in which the component (A) is contained in a dispersion medium, and the component (B) is a dispersoid.

In other words, the composition of the present invention comprises the above components (A) and (B), wherein the component (B) is dispersed in a dispersion medium (continuous phase) that contains the component (A).

In the composition of the present invention, the component (A) is contained in a continuous phase in which at least liposomes are dispersed. Moreover, the component (A) is preferably contained not only in the continuous phase, but also in the liposomes. The component (A) to be contained in the liposomes is more preferably tocopherol. The component (A) can be incorporated into the liposomes by using it in combination with a phospholipid, a polyunsaturated fatty acid, etc., as starting materials for preparing the liposomes.

When contained either in the continuous phase or in the liposomes, the tocopherol used in the present invention is preferably selected from the group consisting of α-tocopherol, β-tocopherol, γ-tocopherol, δ-tocopherol, dl-α-tocopherol acetate, dl-α-tocopherol, and d-α-tocopherol acetate. These tocopherols can be used singly or in combination of two or more. It is more preferable to use one or more of α-tocopherol, β-tocopherol, γ-tocopherol, and δ-tocopherol, which are naturally present tocopherols. In particular, δ-tocopherol is most preferable among these tocopherols, because high effects can be obtained.

The tocopherol content is preferably about 0.005 to 0.5 mass %, and more preferably about 0.01 to 0.1 mass %, based on the total weight of the composition of the present invention. The effect of the present invention can be further exhibited at a tocopherol content of 0.005 mass % or more. Moreover, the effect can be effectively obtained at a tocopherol content of 0.5 mass % or less (that is, when the tocopherol content is greater than 0.5 mass %, the obtained effect may be low despite the high content of tocopherol).

In the present invention, the liposomes contain a polyunsaturated fatty acid. The polyunsaturated fatty acid used in the present invention preferably has 18 to 22 (18, 19, 20, 21, or 22) carbon atoms. Also preferred are polyunsaturated fatty acids having 2 to 6 (2, 3, 4, 5, or 6) double bonds. More preferred are polyunsaturated fatty acids having 18 to 22 carbon atoms and 2 to 6 double bonds. Specific examples thereof include linoleic acid, α-linolenic acid, γ-linolenic acid, dihomo-γ-linolenic acid, arachidonic acid, eicosapentaenoic acid, docosahexaenoic acid, and the like. In addition, salts of polyunsaturated fatty acids can also be used in the present invention. Examples thereof include polyunsaturated fatty acid metal salts, such as polyunsaturated fatty acid sodium salts and polyunsaturated fatty acid potassium salts; polyunsaturated fatty acid amino acid salts, such as polyunsaturated fatty acid arginine salts and polyunsaturated fatty acid lysine salts; polyunsaturated fatty acid amine salts, such as polyunsaturated fatty acid triethanolamine salts and polyunsaturated fatty acid monoethanolamine salts; and the like. Specific examples of salts of polyunsaturated fatty acids include linoleic acid sodium salts, α-linolenic acid potassium salts, etc.; linoleic acid arginine salts, α-linolenic acid lysine salts, etc.; and linoleic acid triethanolamine salts, α-linolenic acid monoethanolamine salts, etc.

Furthermore, in the present invention, a polyunsaturated fatty acid derivative can also be used in place of or in addition to the polyunsaturated fatty acid. Preferred examples of the derivative include monoesters and diesters of polyunsaturated fatty acids, such as ethyl linoleate, ethyl α-linolenate, linoleic acid monoglyceride, α-linolenic acid monoglyceride, linoleic acid diglyceride, and α-linolenic acid diglyceride.

Particularly preferred among these are linoleic acid, α-linolenic acid, ethyl linoleate, ethyl α-linolenate, linoleic acid monoglyceride, and α-linolenic acid monoglyceride; among which linoleic acid is most preferred. Polyunsaturated fatty acids or derivatives thereof can be used singly or in combination of two or more. The content of such a polyunsaturated fatty acid or a derivative thereof is preferably 0.01 to 1 mass %, more preferably 0.05 to 0.5 mass %, even more preferably 0.08 to 0.2 mass %, and still more preferably 0.09 to 0.11 mass %, based on the total weight of the composition of the present invention. When the content of the polyunsaturated fatty acid or derivative thereof is 0.01 mass % or more, whitening effects can be obtained more efficiently by using the composition of the present invention. In contrast, when the content is 1 mass % or lower, there is less risk that the composition will generate a nasty smell or undergo discoloration over time, and that effects that match the polyunsaturated fatty acid content will not be obtained.

The liposomes used in the present invention preferably contain lecithin as a component (particularly membrane component). Examples of lecithin include soybean lecithin, corn lecithin, cottonseed-oil lecithin, yolk lecithin, egg white lecithin, and the like. Further, a lecithin derivative can also be used in place of or in addition to lecithin. Examples of lecithin derivatives include hydrogenated lecithin, and compounds obtained by introducing polyethylene glycol, aminoglycans, etc., into phospholipids of an aforementioned lecithin. Among these, soybean lecithin, yolk lecithin, hydrogenated soybean lecithin, and hydrogenated yolk lecithin are preferred; and soybean lecithin and yolk lecithin are particularly preferred. Furthermore, purified lecithin obtained by increasing the purity of phospholipids (e.g., phosphatidylcholine, phosphatidylserine, phosphatidylethanolamine, phosphatidylinositol, phosphatidylglycerol, and sphingomyelin) present in lecithin can also be preferably used. These lecithins or lecithin derivatives can be used singly or in combination of two or more.

The composition of the present invention can be produced by, for example, preparing a liposome dispersion in which liposomes containing a polyunsaturated fatty acid or a derivative thereof (component (B)) are dispersed in a liquid dispersion medium, and adding the component (A) to the continuous phase of the liposome dispersion. Water can be generally used as the dispersion medium of the liposome dispersion. When the dispersion medium of the liposome dispersion is water, and when the component (A) is a poorly water-soluble substance (tocopherol), the component (A) may be dispersed in the water or dissolved in the water together with a surfactant. In the present invention, the component (A) is preferably dissolved in the dispersion medium.

The method for producing the liposome dispersion is not particularly limited, and standard methods can be used. Examples of such methods are as follows:

(1) a method for producing liposomes by homogeneously mixing a phospholipid, a polyunsaturated fatty acid or a derivative thereof, and other components to be contained, and hydrating the resulting mixture with an aqueous solution containing a pH adjuster, a polyhydric alcohol, sugars, etc.;

(2) a method for producing liposomes by dissolving a phospholipid, a polyunsaturated fatty acid or a derivative thereof, and other components to be contained, in an alcohol, polyhydric alcohol, or the like, and hydrating the resulting mixture with an aqueous solution containing a pH adjuster, a polyhydric alcohol, sugars, etc.;

(3) a method for producing liposomes by forming a complex of a phospholipid, a polyunsaturated fatty acid or a derivative thereof, and other components to be contained, in water using ultrasonic waves, a French press, a homogenizer, or the like; and (4) a method for producing liposomes by mixing and dissolving a phospholipid, a polyunsaturated fatty acid or a derivative thereof, and other components to be contained, in ethanol, and adding the resulting ethanol solution to a potassium chloride aqueous solution, followed by removal of the ethanol.

The liposome dispersion may contain a polymer, a protein and hydrolysate thereof, mucopolysaccharides, etc. That is, the liposome dispersion may be produced by using a polymer, protein, protein hydrolysate, mucopolysaccharides, etc., as materials. Examples of the polymer to be mixed into the liposome dispersion include, but are not limited to, a carboxy vinyl polymer, xanthan gum, sodium alginate, and the like. Preferred among them are a carboxy vinyl polymer and xanthan gum, and particularly preferred is xanthan gum. These polymers can be used singly or in combination of two or more. The polymer content is, but not particularly limited to, 0.001 to 20 mass %, preferably 0.01 to 10 mass %, and particularly preferably 0.05 to 5 mass %, based on the entire liposome dispersion. Examples of the protein and hydrolysate thereof include collagen, elastin, keratin, casein, and other proteins; hydrolysates of these proteins; salts of the hydrolysates; esters of the hydrolysates; and enzyme-treated products of the hydrolysates. The content of the protein and hydrolysate thereof is, but not particularly limited to, 0.001 to 5 mass %, and preferably 0.01 to 1 mass %, based on the entire liposome dispersion. Examples of the mucopolysaccharides include chondroitin sulfate, hyaluronic acid, dermatan sulfate, heparan sulfate, mucoitinsulfuric acid, heparin and derivatives thereof, and salts thereof; among which chondroitin sulfate, hyaluronic acid, and sodium salts thereof are particularly preferred. The mucopolysaccharide content is, but not particularly limited to, 0.0005 to 5 mass %, and preferably 0.001 to 1 mass %, based on the entire liposome dispersion.

The composition of the present invention can be produced by incorporating the component (A) into the continuous phase of the liposome dispersion, as described above. In addition, components other than the component (A) may also be incorporated into the continuous phase of the liposome dispersion within a range that does not impair the effect of the present invention.

For example, when the dispersion medium of the liposome dispersion is water, and when the component (A) is a poorly water-soluble substance (tocopherol), as described above, a surfactant may be further added and dissolved in the continuous phase (i.e., the water, which is the dispersion medium) of the dispersion.

Preferred examples of the surfactant include nonionic surfactants, such as polyoxyethylene alkyl ether, polyoxyethylene fatty acid ester, polyoxyethylene sorbitan fatty acid ester, polyoxyethylene hydrogenated castor oil, and polyglycerol fatty acid ester surfactants. Preferred among them are hexaglycerol fatty acid esters and decaglycerol fatty acid esters, such as hexaglycerol monolaurate, hexaglycerol monomyristate, hexaglycerol monostearate, hexaglycerol monooleate, decaglycerol monolaurate, decaglycerol monooleate, decaglycerol monolinoleate, and decaglycerol monoisostearate. These surfactants can be used singly or in combination of two or more.

Moreover, L-cystine and/or L-threonine may be contained (preferably dissolved) in the continuous phase of the liposome dispersion. The use of L-cystine and L-threonine in the "composition comprising a component (A) and a component (B), the component (B) being dispersed in a continuous phase that contains the component (A)" is preferable because they can further increase the stability of the polyunsaturated fatty acid.

L-cystine and L-threonine can be used singly or in combination in the present invention; however, it is preferable to use them in combination, because a higher effect can be obtained. The amount of L-cystine and L-threonine is preferably 0.0001 to 0.2 mass %, more preferably 0.0005 to 0.1 mass %, and even more preferably 0.001 to 0.06 mass %, based on the total weight of the composition of the present invention.

When the present invention is used as a composition for external use, components that can be generally used in the production of compositions for external use can also be used (contained in the continuous phase of the liposome dispersion). Examples of such components include moisturizers, water-soluble polymers, oil components, coloring agents, antioxidants, sequestering agent, preservatives, pH adjusters, refrigerants, flavoring agents, UV absorbing and scattering agents, antioxidants, medicinal properties, and the like.

Examples of moisturizers include polyols, such as propylene glycol, 1,3-butylene glycol, and glycerol; high-molecular-weight polysaccharides, plant extract, microorganism metabolites, and the like. These moisturizers can be used singly or in combination of two or more.

Examples of water-soluble polymers include cellulose derivatives, carboxy vinyl polymers, xanthan gum, polyvinyl pyrrolidone, (acrylates/steareth-20 itaconate) copolymers, (acrylates/C10-30 alkyl acrylate) crosspolymers, (acrylates/palmeth-25 acrylate) copolymers, (acrylates/ceteth-20 itaconate) copolymers, (acrylates/C12-22 alkyl methacrylate) copolymers, (acrylates/beheneth-25 methacrylate) copolymers, (acrylates/steareth-20 methacrylate) crosspolymers, agar, pectin, gellan gum, gelatin, clay mineral, and the like. These water-soluble polymers can be used singly or in combination of two or more.

Examples of oil components include animal oil, vegetable oil, mineral oil, hydrocarbon oil, ester oil, waxes, higher alcohol, higher fatty acid, silicone oil and derivatives thereof, Vaseline, essential oil, and the like. These oil components can be used singly or in combination of two or more.

Furthermore, when the present invention is used as a composition for external use, components that can generally be contained in liposomes can also be used in the preparation of liposomes within a range that does not impair the effect of the present invention. Examples thereof include antioxidants, such as ascorbic acid; organic acids, such as lactic acid and citric acid; lipids, such as phosphatidylglycerol and phosphatidylethanolamine; natural polymers, such as chitosan, fucoidan, and hyaluronic acid; synthetic polymers, such as polyethylene glycol and carboxy vinyl polymer; sugars, such as trehalose, lactulose, and maltitol; polyols, such as glycerol; and the like.

The composition of the present invention is preferably used as a composition for external use (a composition to be applied to the skin). Examples of compositions for external use include pharmaceutical compositions, quasi-drug compositions, and cosmetic compositions. It is particularly preferable to use the composition of the present invention as a composition for external use having a skin-whitening effect (i.e., a skin-whitening composition for external use) in the form of a drug, quasi drug, or cosmetic. The dosage form of the composition is not particularly limited. Examples of the dosage form include face packs, paste, ointment, cream, gel, lotion, emulsion, essence, face lotion, spray, and the like.

When the composition of the present invention is used as a composition for external use, the target of application is not particularly limited, but is preferably a human who wants to whiten the skin.

The present invention also includes a method for whitening skin (skin-whitening method) comprising the step of applying the composition of the present invention to the target skin. This method can be used, for example, for therapeutic and cosmetic purposes. That is, the skin-whitening method includes therapeutic and cosmetic methods for skin whitening. More specifically, the whitening method as mentioned herein can be used, for example, for the treatment of spots, dullness, melasma, post-inflammatory hyperpigmentation, etc., or for cosmetic purposes. The application target and application dose are as described above.

EXAMPLES

Examples of the present invention are described below; however, the present invention is not limited to the following Examples. "%" denotes "mass %" unless otherwise specified.

Test of Stability Over Time of Polyunsaturated Fatty Acid

A dispersion of linoleic acid-containing liposomes was prepared in the manner disclosed in Example 3 of JP11-1423A. More specifically, soybean lecithin, linoleic acid, and dl-α-tocopherol were homogeneously mixed with 1,3-butylene glycol, and purified water was added thereto. The resulting mixture was treated with a French press, thereby preparing a liposome dispersion (linoleic acid content: 0.5% or 1.0%). The amount of each component used in the preparation was such that the soybean lecithin content was 4 mass %, the dl-α-tocopherol content was 0.05 mass %, and the 1,3-butylene glycol content was 4 mass %, based on the total weight of the liposome dispersion.

Then, according to the formulations shown in Table 1 below, components were mixed to produce compositions (Examples and Comparative Examples). The "other components" in Table 1 were the same in all examples. The breakdown of the "other components" is given in Table 2. The numerical value of each component in Table 1 and 2 shows their amount (mass %).

Comparative Example 1 shows a case where only L-cystine and L-threonine are used without the addition of tocopherol and phytic acid. Comparative Example 2 shows a case where an oil-soluble licorice extract, which is known to have antioxidant properties, is used in place of tocopherol or phytic acid.

Further, the compositions were allowed to stand at 40° C. for 2 months after production. Then, the amount of linoleic acid in each composition was quantified to examine the stability of linoleic acid in each composition. The quantitative determination of linoleic acid was performed by a high-performance liquid chromatography (1100 series, produced by Agilent). The residual ratio of linoleic acid was calculated from the quantitative values after being left, based on blending theory values. The residual ratio of linoleic acid after being left at 40° C. for 2 months was evaluated as follows: compositions with a residual ratio of linoleic acid of 95% or more: A; 90% or more and less than 95%: B; less than 90%: C. Table 1 also shows the results.

TABLE 1

| Component name | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Linoleic acid-containing liposome dispersion (linoleic acid content: 0.5%) | — | 20 | — | 20 | 20 | — | 20 | — | 20 |
| Linoleic acid-containing liposome dispersion (linoleic acid content: 1%) | 10 | — | 10 | — | — | 10 | — | 10 | — |
| dl-α-tocopherol acetate | 0.06 | — | — | — | — | — | — | 0.01 | 0.03 |
| Natural vitamin E (α-, β-, γ-, δ-mixed product) | — | 0.06 | — | — | — | — | — | — | — |
| δ-tocopherol | — | — | 0.01 | 0.03 | 0.06 | 0.09 | — | — | — |
| Phytic acid | — | — | — | — | — | — | 0.025 | 0.02 | 0.01 |
| L-cystine | — | — | — | — | — | — | — | — | — |
| L-threonine | — | — | — | — | — | — | — | — | — |
| Oil-soluble licorice extract | — | — | — | — | — | — | — | — | — |
| Other components (see Table 2 for breakdown) | 13.4 | 13.4 | 13.4 | 13.4 | 13.4 | 13.4 | 13.4 | 13.4 | 13.4 |
| Water | Balance | Balance | Balance | Balance | Balance | Balance | Balance | Balance | Balance |
| Total | 100 | 100 | 100 | 100 | 100 | 100 | 100 | 100 | 100 |
| pH | 7.38 | 7.2 | 7.50 | 6.96 | 6.79 | 6.96 | 7.22 | 7.27 | 7.34 |
| Residual ratio after being left at 40° C. for 2 months (%) | 93 | 94 | 95 | 97 | 98 | 99 | 99 | 98 | 95 |
| Stability evaluation of linoleic acid | B | B | A | A | A | A | A | A | A |

| Component name | Ex. 10 | Ex. 11 | Ex. 12 | Ex. 13 | Ex. 14 | Ex. 15 | Ex. 16 | Comp. Ex. 1 | Comp. Ex. 2 |
|---|---|---|---|---|---|---|---|---|---|
| Linoleic acid-containing liposome dispersion (linoleic acid content: 0.5%) | — | — | — | 20 | — | — | 20 | 20 | 20 |

TABLE 1-continued

| | | | | | | | | | |
|---|---|---|---|---|---|---|---|---|---|
| Linoleic acid-containing liposome dispersion (linoleic acid content: 1%) | 10 | 10 | 10 | — | 10 | 10 | — | — | — |
| dl-α-tocopherol acetate | 0.03 | 0.03 | 0.03 | 0.03 | 0.05 | — | — | — | — |
| Natural vitamin E (α-, β-, γ-, δ-mixed product) | — | — | — | — | — | — | — | — | — |
| δ-tocopherol | — | — | — | — | — | 0.015 | 0.03 | — | — |
| Phytic acid | 0.005 | 0.015 | 0.025 | — | 0.015 | 0.005 | — | — | — |
| L-cystine | — | — | — | 0.001 | — | — | 0.001 | 0.001 | — |
| L-threonine | — | — | — | 0.002 | — | — | 0.02 | 0.02 | — |
| Oil-soluble licorice extract | — | — | — | — | — | — | — | — | 0.06 |
| Other components (see Table 2 for breakdown) | 13.4 | 13.4 | 13.4 | 13.4 | 13.4 | 13.4 | 13.4 | 13.4 | 13.4 |
| Water | Balance | Balance | Balance | Balance | Balance | Balance | Balance | Balance | Balance |
| Total | 100 | 100 | 100 | 100 | 100 | 100 | 100 | 100 | 100 |
| pH | 7.33 | 7.15 | 7.02 | 7.03 | 7.45 | 7.36 | 7.44 | 7.47 | 6.9 |
| Residual ratio after being left at 40° C. for 2 months (%) | 98 | 98 | 97 | 95 | 99 | 97 | 99 | 88 | 84 |
| Stability evaluation of linoleic acid | A | A | A | A | A | A | A | C | C |

TABLE 2

| | |
|---|---|
| Polyglyceryl-10 laurate | 0.4 |
| Pentaerythrityl tetraoctanoate | 0.5 |
| Glycerol | 1 |
| 1,3-butylene glycol | 3.5 |
| Olive oil | 1.5 |
| Squalane | 2.5 |
| Dimethicone | 0.25 |
| Carbomer | 0.7 |
| L-ascorbic acid 2-glucoside | 2 |
| Methylparaben | 0.2 |
| Potassium hydroxide | 0.8 |
| Flavoring | 0.05 |
| Total | 13.4 |

Table 1 demonstrated that the stability of linoleic acid in the composition containing an oil-soluble licorice extract (Comparative Example 2) was poor. It was also found that among the compositions containing tocopherol alone, those containing dl-α-tocopherol acetate had a higher effect of stabilizing linoleic acid than those containing natural vitamin E or δ-tocopherol. It was further found that the compositions containing L-cystine and L-threonine in combination with tocopherol had a higher effect of stabilizing linoleic acid than those containing tocopherol alone.

Formulation Examples of the compositions of the present invention are shown below. "%" denotes "mass %" unless otherwise specified. All components contained in the liposome dispersion, other than liposomes, are contained in the continuous phase.

TABLE 3

Formulation Example 1: Essence

| Component | Amount (%) |
|---|---|
| Linoleic acid-containing liposome dispersion (linoleic acid content: 1%) | 20 |
| d-δ-tocopherol | 0.08 |
| L-threonine | 0.03 |
| L-cystine | 0.01 |

TABLE 3-continued

Formulation Example 1: Essence

| Component | Amount (%) |
|---|---|
| 1,3-butylene glycol | 5 |
| Olive oil | 3 |
| Glycerol | 2 |
| Ascorbic acid glucoside | 2 |
| Squalane | 1.5 |
| (Acrylates/steareth-20 itaconate) copolymer | 1.5 |
| Decaglycerol monolaurate | 1 |
| Hazelnut oil | 0.5 |
| Cholesteryl hydroxystearate | 0.4 |
| Methylpolysiloxane | 0.3 |
| Paraben | 0.1 |
| Phenoxyethanol | 0.1 |
| Xanthan gum | 0.05 |
| Potassium hydroxide | Suitable amount |
| Purified water | Balance |
| Total | 100 |

TABLE 4

Formulation Example 2: Emulsion

| Component | Amount (%) |
|---|---|
| Linoleic acid-containing liposome dispersion (linoleic acid content: 0.5%) | 16 |
| γ-tocopherol | 0.05 |
| L-threonine | 0.02 |
| 1,3-butylene glycol | 5 |
| Olive oil | 4 |
| Squalane | 4 |
| Polyoxyethylene cetyl ether | 0.5 |
| Methylpolysiloxane | 0.5 |
| Pentaerythrityl tetraoctanoate | 0.5 |
| Paraben | 0.2 |
| Carboxyvinyl polymer | 0.2 |
| Dipotassium glycyrrhizinate | 0.1 |

TABLE 4-continued

Formulation Example 2: Emulsion

| Component | Amount (%) |
|---|---|
| Flavoring | 0.1 |
| Potassium hydroxide | Suitable amount |
| Purified water | Balance |
| Total | 100 |

TABLE 5

Formulation Example 3: Cream

| Component | Amount (%) |
|---|---|
| α-linolenic acid-containing liposome dispersion (α-linolenic acid content: 1.0%) | 5 |
| dl-α-tocopherol acetate | 0.05 |
| Phytic acid | 0.005 |
| Glycerol | 10 |
| Meadowfoam oil | 8 |
| Squalane | 6 |
| Dipropylene glycol | 5 |
| Ascorbyl tetraisopalmitate | 3 |
| Lipophilic glyceryl monostearate | 2 |
| Cetanol | 2 |
| Polyglyceryl monostearate | 1 |
| Decamethylcyclopentasiloxane | 1 |
| Behenyl alcohol | 0.3 |
| (Acrylates/C10-30 alkyl acrylate) crosspolymer | 0.4 |
| Potassium hydroxide | Suitable amount |
| Purified water | Balance |
| Total | 100 |

The invention claimed is:

1. A composition comprising a component (A) and a component (B), the component (B) being dispersed in a continuous phase that contains the component (A):
    (A) at least one member selected from the group consisting of tocopherol and phytic acid; and
    (B) liposomes containing a polyunsaturated fatty acid having 18 to 22 carbon atoms or a derivative thereof,
    wherein the amount of component (A) improves stability of the polyunsaturated fatty acid or derivative thereof in component (B).

2. The composition according to claim 1, wherein the continuous phase contains at least δ-tocopherol.

3. The composition according to claim 1, wherein the continuous phase further contains at least one member selected from the group consisting of L-cystine and L-threonine.

4. The composition according to claim 1, wherein the liposomes also contain at least one member selected from the group consisting of tocopherol and phytic acid.

5. The composition according to claim 1, which is a composition to be used externally.

6. The composition according to claim 1, wherein the tocopherol is at least one member selected from the group consisting of α-tocopherol, β-tocopherol, γ-tocopherol, δ-tocopherol, dl-α-tocopherol acetate, dl-α-tocopherol, and d-α-tocopherol acetate.

7. The composition according to claim 1, wherein the continuous phase contains at least phytic acid.

* * * * *